United States Patent
Morgan et al.

(10) Patent No.: US 9,243,278 B2
(45) Date of Patent: Jan. 26, 2016

(54) MECHANOTRANSDUCTION BY THE SYNERGISTIC ACTION OF HETEROTYPIC CELL INTERACTIONS

(71) Applicant: Brown University, Providence, RI (US)

(72) Inventors: Jeffrey R Morgan, Sharon, MA (US); Toni-Marie Achilli, Providence, RI (US); Jacquelyn Youssef Schell, Providence, RI (US)

(73) Assignee: Brown University, Providence, RI (US)

( * ) Notice: Subject to any disclaimer, the term of this patent is extended or adjusted under 35 U.S.C. 154(b) by 367 days.

(21) Appl. No.: 13/623,668

(22) Filed: Sep. 20, 2012

(65) Prior Publication Data

US 2013/0109625 A1 May 2, 2013

Related U.S. Application Data

(60) Provisional application No. 61/538,067, filed on Sep. 22, 2011.

(51) Int. Cl.
*C12Q 1/02* (2006.01)
*G01N 33/50* (2006.01)

(52) U.S. Cl.
CPC ............ *C12Q 1/025* (2013.01); *G01N 33/5008* (2013.01)

(58) Field of Classification Search
USPC ................................ 435/4, 7.2, 29; 424/130.9
See application file for complete search history.

(56) References Cited

U.S. PATENT DOCUMENTS

| | | | |
|---|---|---|---|
| 5,650,164 | A | 7/1997 | Della Valle et al. |
| 5,792,653 | A | 8/1998 | Weibezahn et al. |
| 7,887,843 | B2 | 2/2011 | Libera et al. |
| 8,361,781 | B2 | 1/2013 | Morgan et al. |
| 8,501,476 | B2 | 8/2013 | Morgan et al. |
| 2003/0153078 | A1 | 8/2003 | Libera et al. |
| 2004/0009537 | A1* | 1/2004 | Roos et al. .......... G01N 33/6872 435/7.2 |
| 2005/0084843 | A1* | 4/2005 | Sheetz et al. ...................... 435/4 |
| 2005/0169962 | A1 | 8/2005 | Bhatia et al. |
| 2009/0258006 | A1* | 10/2009 | Weiss et al. ................. 424/130.1 |
| 2013/0079288 | A1 | 3/2013 | Morgan et al. |
| 2013/0137155 | A1 | 5/2013 | Morgan et al. |

FOREIGN PATENT DOCUMENTS

| | | |
|---|---|---|
| DE | 4132379 A1 | 4/1993 |
| EP | 1 367 119 B1 | 9/2008 |
| JP | 08-140673 A | 6/1996 |
| JP | 2000-069957 A | 3/2000 |
| JP | 2003-052361 A | 2/2003 |
| JP | 2004-089136 A | 3/2004 |
| JP | 2004-097047 A | 4/2004 |
| JP | 2004-121168 A | 4/2004 |
| JP | 2005-160596 A | 6/2005 |
| JP | 2006-055069 A | 3/2006 |
| WO | WO 95/31184 A1 | 11/1995 |
| WO | WO 99/52356 A1 | 10/1999 |
| WO | WO 03/059072 A1 | 7/2003 |
| WO | WO 2005/077013 A2 | 8/2005 |
| WO | WO 2007/087402 A2 | 8/2007 |

OTHER PUBLICATIONS dictionary.com. Myofibroblast. Definition retrieved from the dictionary.com website on Nov. 16, 2014: <http://dictionary.reference.com/browse/myofibroblast>.*
Dean, D. M., et al., "Rods, tori, and honeycombs: the directed self-assembly of microtissues with prescribed microscale geometries," *FASEB J.*, 21(14): 4005-4012 (2007).
English Translation of JP 2006-055069, downloaded from http://www4.ipdl.inpit.go.jp on Nov. 2, 2011.
Extended European Search Report from European Application No. 07762405.4, "Cell Aggregation and Encapsulation Device and Method." Date of Mailing: Sep. 22, 2009; 7 pages.
Folch, A., and Toner, M., "Microengineering of Cellular Interactions," *Annu. Rev. Biomed. Eng.*, 2(1): 227-256 (2000).
Fukuda, J., and Nakazawa, K., "Orderly Arrangement of Hepatocyte Spheroids on a Microfabricated Chip," *Tissue Engineering*, 11(7/8): 1254-1262 (2005).
International Search Report and Written Opinion of the International Searching Authority from International Application No. PCT/US2007/002050, "Cell Aggregation and Encapsulation Device and Method". Date of Mailing: Oct. 9, 2008; 5 pages.
Jakab, K., et al., "Engineering biological structures of prescribed shape using self-assembling multicellular systems," *Proc. Natl. Acad. Sci. USA*, 101(9): 2864-2869 (2004).
Kelm, J. M., et al., "Tissue-Transplant Fusion and Vascularization of Myocardial Microtissues and Macrotissues Implanted into Chicken Embryos and Rats," *Tissue Engineering*, 12(9): 2541-2553 (2006).
Kelm, J. M., and Fussenegger, M., "Microscale tissue engineering using gravity-enforced cell assembly," *TRENDS in Biotechnology*, 22(4): 197-202 (2004).

(Continued)

*Primary Examiner* — Kagnew H Gebreyesus
*Assistant Examiner* — Nghi Nguyen
(74) *Attorney, Agent, or Firm* — Hamilton, Brook, Smith & Reynolds, P.C.

(57) ABSTRACT

The candidates are screened and then employed by administering to patients in need thereof of a drug candidate that affects heterotypic intercellular mechanotransduction. At least two types of cells are labeled with distinct intracellular fluorescent marker labels and combined to form a cell suspension and cultured to form a microtissue, such as spheroids. The cells or the spheroids are combined with a drug candidate, either before, during or after forming the spheroids. The distribution of the different cell types is compared to that of essentially the same suspension culture in the absence of the drug candidate. Alternatively, the cell power of cells cultured in a non-adherent mold that determines at least in part, the shape of microtissue formed is measured and compared with essentially the same cell suspension cultured in the same manner in the absence of a drug candidate. A patient in need thereof can be administered a drug identified as affecting heterotypic intercellular mechanotransduction. Alternatively, a macrotissue can be formed that is employed in therapeutic treatment of a patient in need thereof.

6 Claims, 12 Drawing Sheets
(10 of 12 Drawing Sheet(s) Filed in Color)

(56) References Cited

OTHER PUBLICATIONS

Livoti, C. M. and Morgan, J. R., "Self-Assembly and Tissue Fusion of Toroid-Shaped Minimal Building Units," *Tissue Engineering: Part A*, 16(6): 2051-2061 (2010).

Mironov, V., et al., "Organ printing: computer-aided jet-based 3D tissue engineering," *TRENDS in Biotechnology*, 21(4): 157-161 (2003).

Napolitano, A. P., et al., "Dynamics of the Self-Assembly of Complex Cellular Aggregates on Micromolded Nonadhesive Hydrogels," *Tissue Engineering*, 13(8): 2087-2094 (2007).

Napolitano, A. P., et al., "Scaffold-free three-dimensional cell culture utilizing micromolded nonadhesive hydrogels," *BioTechniques*, 43(4): 494-500 (2007).

Rago, A. P., et al., "Miniaturization of an Anoikis assay using non-adhesive micromolded hydrogels," *Cytotechnology*, 56(2): 81-90 (2008).

Rago, A. P., et al., "Controlling Cell Position in Complex Heterotypic 3D Microtissues by Tissue Fusion," *Biotechnology and Bioengineering*, 102(4): 1231-1241 (2009).

Yeh, J., et al., "Micromolding of shape-controlled, harvestable cell-laden hydrogels," *Biomaterials*, 27(31): 5391-5398 (2006).

Office Action from U.S. Appl. No. 12/896,173, mailing date Jun. 14, 2012.

* cited by examiner

MECHANOTRANSDUCTION BY THE SYNERGISTIC ACTION OF HETEROTYPIC CELL INTERACTIONS

RELATED APPLICATION

This application claims the benefit of U.S. Provisional Application No. 61/538,067, filed on Sep. 22, 2011. The entire teachings of the above application are incorporated herein by reference.

GOVERNMENT SUPPORT

This invention was made with government support under DMR-0520651, DMI-0506661, and CMMI-0825185 awarded by the National Science Foundation and under R01EB008664-01A1 awarded by the National Institutes of Health. The government has certain rights in the invention.

BACKGROUND OF THE INVENTION

Cell-cell interactions are of wide fundamental importance to a myriad of processes that occur during development, wound healing, and metastasis. In addition to generating biochemical signals that trigger intracellular cascades, it is becoming increasingly clear that cell-cell interactions generate and sense mechanical forces and that these processes are equally important for controlling the behavior of cells and the surrounding tissue (1). This field of mechanotransduction is examining the effects of various mechanical forces including adhesive forces (e.g., cadherins) and tensile forces, (e.g., myosin contraction) as well as the effects of the stiffness of cell types and their surrounding extracellular matrix (ECM). Mechanical forces may not only mediate cell signaling, but also direct morphogenesis, cell migration and may be altered in certain disease states, such as metastasis and fibrosis (2-8).

An assay to quantify the collective forces that drive cell aggregation and the self-assembly of 3D microtissues can be employed (9). This assay measure the self-assembly of a multi-cellular toroid on a cone and it quantifies cell power, the work performed by a toroid as it moves up the nonadhesive cone against the force of gravity. This complex process may be driven by numerous factors including the number of surface adhesion proteins, cytoskeletal motors, and metabolic rate. Conversely, it is possible that self-assembly is opposed by other factors, such as cell stiffness, intransient receptor binding and other sources of friction.

Therefore, a need exists for a method and system that overcomes or minimizes the complexities and other problems of the above-referenced techniques.

SUMMARY OF THE INVENTION

The invention generally is directed to a method for screening drug candidates that affect heterotrophic intercellular mechanical transduction and to methods for employing drugs identified by the screening method.

In one embodiment, the method includes labeling at least two types of cells with distinct intracellular fluorescent marker labels and seeding cell culture medium with the at least two types of cells in a suspension. The cells are cultured in a non-adherent mold to thereby form spheroids, and combined with a drug candidate either before, during or after they are cultured to form the spheroids and combined with a drug candidate either before, during or after they are cultured to form the spheroids. The distribution of the at least two different types of cells to that of spheroids is compared to that of spheroids of essentially the same suspension culture in the absence of the drug candidate. Optionally, a drug candidate that is determined by the comparison to affect heterotypic intracellular-mechanotransduction is administered to a patient in need thereof.

In another embodiment, the method includes seeking a non-adherent mold with at least two types of cells in suspension. The cells are cultured in the non-adherent mold to thereby form a microtissue, the shape of which is determined, at least in part by the mold. A drug candidate is combined with the cells before, during or after they are cultured to form the microtissue. Cell power of the cells is measured during formation of the microtissue. The measured cell powers compared to that of microtissues forms with mono dispersions of each of the two cell types in the presence of a drug candidate and with a combination of the cell types in the absence of the drug candidate, to thereby determine the effect of the drug that had heterotypic intracellular-mechanotransduction. Optionally, a macrotissue is formed with at least one drug candidate identified as affecting the heterotypic intracellular-mechanotransduction.

In yet another embodiment, the method includes labeling at least two types of cells with distinct intracellular fluorescent marker labels and seeding a cell culture medium with the at least two types of cells in a suspension. The cells are cultured in a non-adherent mold to thereby form a microtissue, the shape of which is determined at least in part by the mold. A drug candidate is combined with the cells before, during or after they are cultured to form the microtissue. The cell power of the cells is measured during formation of the microtissue. The measured cell power is compared to that of microtissues formed with the mono dispersion of each of the two cell types in the presence of the drug candidate and with a combination of the cell types in the absence of the drug candidate, due to thereby determine the effect of the drug candidate on mechanotransduction. The distribution of the at least two different types of cells to that of microtissues of essentially the same cell suspension and cultured in the absence of the drug candidate are compared. Optionally, a patient in need thereof is administered a drug identified by the method that affects mechanotransduction and distribution of the cell types in the microtissue.

The invention measures self-assembly in terms of work performed against gravity in a consistent and well defined environment (i.e., non-adhesive synthetic hydrogel cone of defined geometry). These consistencies in the load and environmental test bed conditions enable precise quantitative comparisons to be made between cell types, as well as the quantification of the contributions of proteins or protein systems to the complex process of cell aggregation. The invention identifies and employs drugs that are useful as therapeutics to treat conditions associated with fibrosis, such as drugs that selectively inhibit the enhanced mechanotransduction that occurs due to heterotypic cell interaction between fibroblasts and parenchymal cells such as liver, lung and kidney cells and the cells of other organs fibrosis. The invention can be used to identify drugs that selectively disrupt the heterotypic cell interface.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 10A, 11B and 12C: Simulation of stress distribution in heterotypic microtissues demonstrates that the heterotypic environment increased stress in the NHF and the surrounding H35s. For the 1:10 ratio (A and B), NHFs (red circles) are randomly distributed with the H35s in a toroid with peg and toroid radii of 325 μm and 675 m, respectively (A and B). The contractility of NHFs results in tension in the NHF, the NHF/H35 heterotypic interfacial region and in the H35. The variation of the tensile stresses near one of the NHFs surrounded by H35s (black square in (A)) is plotted (B). The tension induced by the contractility of NHFs decreases from the interface of the NHF with the surrounding H35s. Note that the tension in the heterotypic interface region is much larger than in the surrounding H35 region (blue). The tensile stresses in homotypic microtissues (C) decrease radially from the peg and are uniform circumferentially. (D) The tensile stresses of heterotypic and homotypic microtissues in the same location (indicated by the black squares) are compared: The black curve corresponds to stresses in the heterotypic tissue, while the red and blue curves represent stresses in homotypic NHF and H35 tissues of the same dimensions. The red and blue shaded regions (D) indicate the enhancement in tension for the NHFs and H35s in the heterotypic tissue, compared to the tension in the corresponding homotypic environments. Tensile stresses we plot correspond to the maximum in-plane principal stress, and are normalized by the elastic modulus of cells. Arrow in (B) denotes the path along which the distance in (D) is measured. The decay of the tension (D) in the heterotypic interface region is consistent with the f-actin distribution shown in FIG. 8A-8D.

FIGS. 11A-11H: NHFs (labeled red) and H35s (labeled green) (1:1) self-assembled a 3D spheroid and self-sorted such that NHFs formed the central core and H35s the outer shell. Fluorescent images at (A) 0 h, (B) 1 h, (C) 2 h, (D) 3 h, (E) 6 h, (F) 9 h, (G) 12 h, and (H) 15 after seeding. Bar=100 microns.

DETAILED DESCRIPTION OF THE INVENTION

Figure 1:
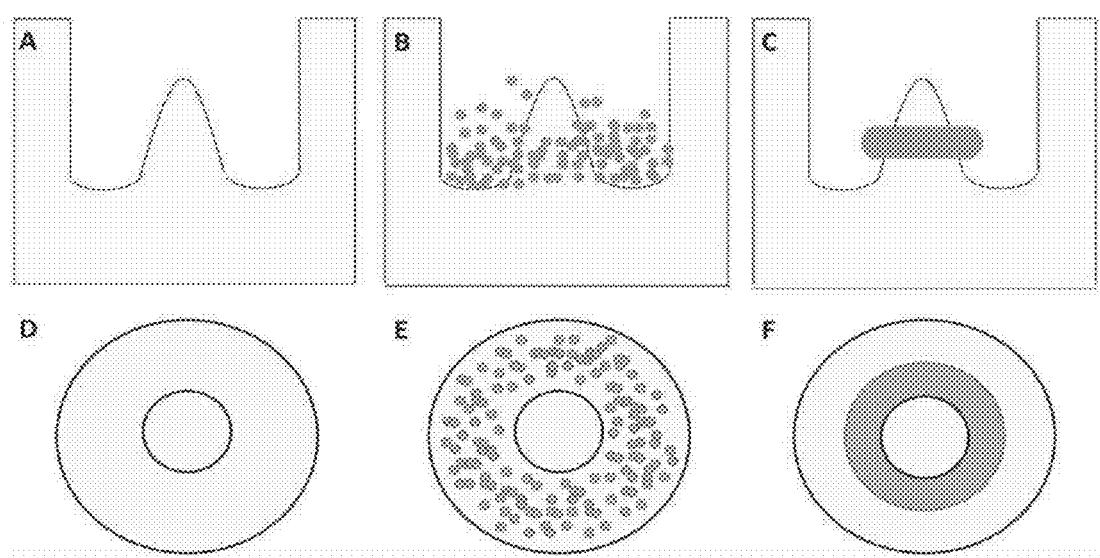
FIGS. 1A-1F: Diagram of side view (A, B, C) and top view (D, E, F) of the multi-cellular toroid on a cone assay used to measure cell power. Micromolded nonadhesive hydrogel with a circular trough and a cone in the center (A, D). Monodispersed cells seeded onto the nonadhesive micromold settle onto the trough (B,E), aggregate and form a multi-cellular toroid that constricts and moves up the nonadhesive cone (C, F). The work performed by this toroid as it moves the mass of the toroid up the cone against the force of gravity is used to calculate cell power as described in Youssef et al. PNAS.
Figure 2:
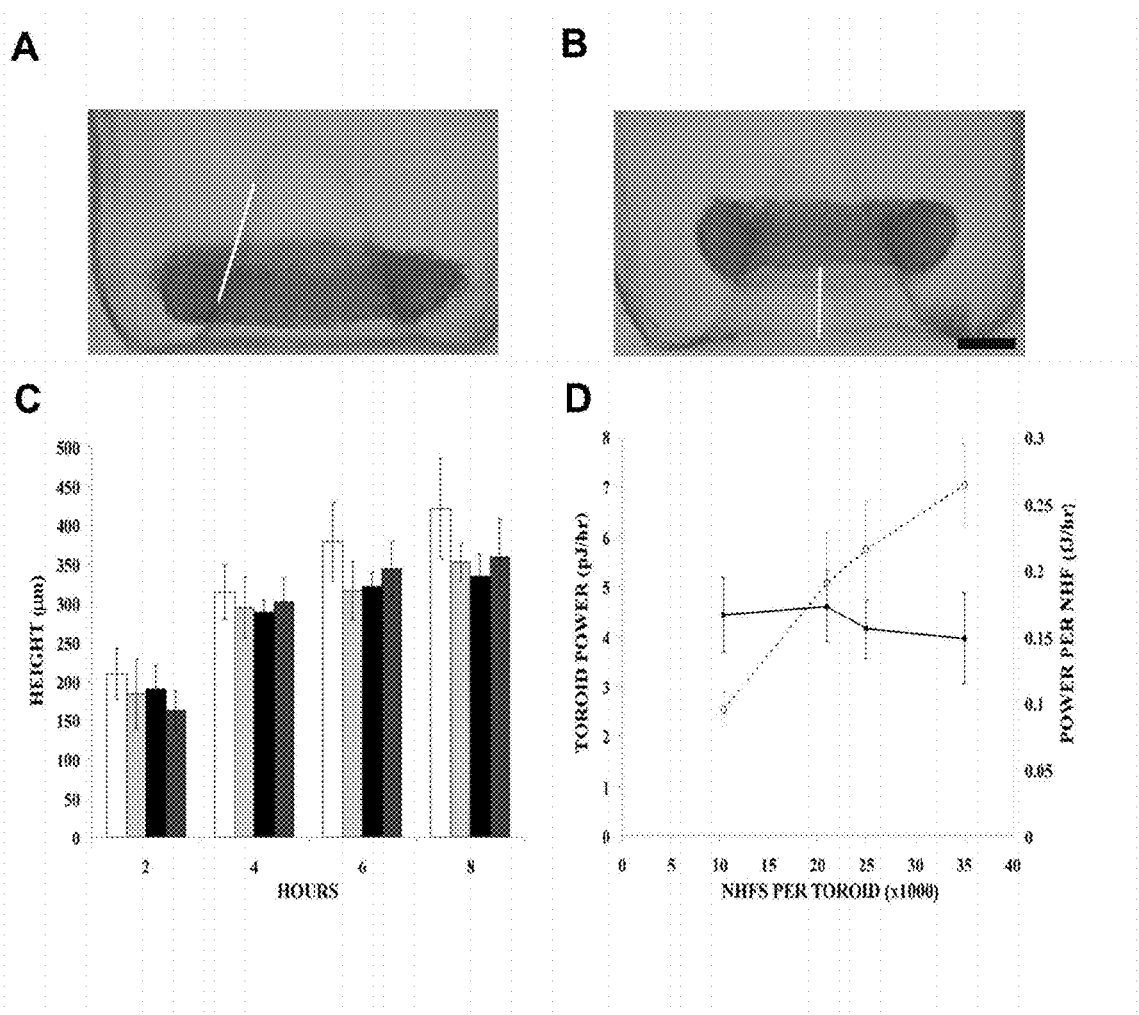
FIGS. 2A-2D: Toroid height and NHF cell power were constant regardless of cell number. NHFs were seeded into toroid micro-molds with increasing cells per toroid. Side view images of the toroids were taken, at 2 (A) and 4 hours (B). As early as 2 hours the toroid had begun to move up the cone (white line added to show slope) and continued up the cone. Toroid height was measured from the bottom of the well to bottom of the toroid at 2 hour intervals for 8 hours for about 10,500 (□); about 21,000 ( ) about 25,000 (■); and about 35,000 (■) cells per toroid (C). Toroid power (open circles) was directly proportional to the number of cells within the toroid ($R^2=0.97$) while cell power (closed circles) was constant over the range of cell numbers tested (p>0.05). n=5, 8, 7, and 4 for the about 10,500; about 21,000; about 25,000; and about 35,000 cells per toroid samples, respectively. Scale bar is 200 μm.

The features and other details of the invention, either as steps of the invention or as a combination of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

In one embodiment, the method includes labeling at least two types of cells with distinct intracellular fluorescent marker labels and seeding cell culture medium with the at least two types of cells in suspension. The cells are cultured in a non-adherent mold to thereby form spheroids. A drug candidate is combined with the cells before, during or after culturing the cells to form the spheroids. The distribution of the at least two different types of cells to that of spheroids is compared to that of spheroids of essentially the same suspension culture in the absence of the drug candidate. Optionally, a drug candidate that is determined by the comparison to affect heterotypic intracellular-mechanotransduction is administered to a patient in need thereof.

In another embodiment, the method includes seeding a non-adherent mold with at least two types of cells in suspension. The cells are cultured in the non-adherent mold to thereby form a microtissue, the shape of which is determined, at least in part, by the mold. A drug candidate is combined with the cells before, during or after culturing the cells to form the microtissue. Cell power of the cells is measured during formation of the microtissue. The measured cell power is compared to that of microtissues formed with monodispersions of each of the two cell types in the presence of a drug candidate and with a combination of the cell types in the absence of the drug candidate, to thereby determine the effect of the drug on heterotypic intracellular-mechanotransduction. Drug candidates can be identified to treat fibrosis, such as drugs that selectively inhibit the enhanced mechanotransduction that occurs due to heterotypic cell interaction between fibroblasts and parenchymal cells such as liver, lung and kidney cells and the cells of other organs fibrosis. The invention can be used to identify drugs that selectively disrupt the heterotypic cell interface.

In yet another embodiment, the method includes labeling at least two types of cells with distinct intracellular fluorescent marker labels and seeding a cell culture medium with the at least two types of cells in a suspension. The cells were cultured in a non-adherent mold to thereby form a microtissue, the shape of which is determined at least in part by the mold. A drug candidate is combined with the cells before, during or after culturing the cells to form the microtissues. The cell power of the cells is measured during formation of the microtissue. The measured cell power is compared to that of microtissues formed with the mixture of the monodispersion of each of the two cell types in the presence of the drug candidate and with a combination of the cell types in the absence of the drug candidate, to thereby determine the effect of the drug candidate on mechanotransduction. The distribution of the at least two different types of cells to that of microtissues of essentially the same cell suspension and cultured in the absence of the drug candidate are compared and a patient in need thereof is administered a drug identified by the method that affects mechanotransduction and distribution of the cell types in the microtissue. In one embodiment, at least one of the cell types is a connective tissue cell. In one embodiment the connective tissue cell is a fibroblast cell. In one embodiment the connective tissue cell is a myofibroblast cell. A macrotissue is formed with at least one drug candidate identified as affecting the heterotypic intracellular-mechanotransduction.

Examples of suitable microtissues include microspheres, toroids, tubules, rods and honeycombs. Examples of suitable non-adherent molds include those having shapes of microspheres, toroids, tubles, rods, honeycombs, and formed of hydrogels In another embodiment at least one of the cell types is a parenchymal cell. Examples of suitable parenchymal cells include epithelial cells, muscle cells, kidney cells, liver cells, lung cells, cardiomyocytes skin and neural cells. Examples of suitable drugs for screening would be used to screen a library of known, as well as unknown drugs to find ones that alter mechanotransduction due to heterotypic cell interactions.

Examples of suitable fluorescent marker labels include Cell Tracker™, Cell Trace™ and stains that are mediated by genetically modifying the cells to express fluorescent proteins.

In another embodiment, the method includes the step of combining the cells with at least one drug identified as affecting intracellular mechanotransduction between the at least two cell types.

Cell-mediated mechanical forces, implicated in tissue remodeling and wound healing, are often the focus of pathological conditions such as fibrosis (15-17). Much work has focused on the contractile forces of cells embedded in an ECM and quantitative studies have helped to define the complex interplay between matrix composition and stiffness and the role of growth factors in regulating contractile forces in 3D analogs (15, 18-20). However in many circumstances, cells exert contractile forces on other cells and yet there is little quantitative understanding of the factors influencing direct cell-cell mechanotransduction. In fact, much of the work with cells in ECM analogs is assumed to be applicable to cell-cell interaction. Here, we quantify the forces of cell-cell interactions and show that the effect of heterotypic cell interactions is significantly greater than the effect of TGF-β1, a well-known inducer of cell contractility.

Monodispersed cells have been seeded onto nonadhesive hydrogels with toroidal shaped recesses where they aggregate and form a multi-cellular toroid that moves up the central cone (21). As can be seen from FIGS. 1A-F, side views, FIGS. 1A-C and respective top views, FIGS. 1D-F, of the multi-cellular toroid on a cone assay is employed to measure cell power. FIGS. 1A and 1D represent a micromolded nonadhesive hydrogel with a circular trough and a cone in the center. Monodispersed cells that are seeded onto the non-adhesive micromold settle into the trough, as shown in FIGS. 1B and 1E. They then aggregate and form a multi-cellular toroid that constricts and moves up the non-adhesive cone of the mold, as shown in FIGS. 1C and 1F. The work performed by this toroid as it moves the mass of the toroid up the cone against the force of gravity is used to calculate cell power as described in Youssef, J., Nurse, A. k, Freund, L. B., and Morgan, J. R. (2011), "Quantification of the Forces Driving Self-Assembly of Three-Dimensional Microtissues," *Proc. Nat'l. Acad. Sci.*

U.S.A. 108, 6993-8, the relevant teachings of which are incorporated by reference in their entirety. The complex cell-cell interactions driving this simple event were quantified in terms of power and shown to vary significantly between cell types. As a tool for quantifying cell-cell aggregation, the toroid/cone assay does not interfere with cell function by altering cells or cell function and requires little if any calibration because it relies only on gravity, a well-characterized external load.

Cell power is a quantitative measure of the multi-component system (mechanical, chemical, and surface energy) that drives toroid motion up the cone. In addition to gravity, the cell power measurement also takes into account all forces (e.g., friction) that oppose the motion of the toroid up the cone. The invention measures self-assembly in terms of work performed against gravity in a consistent and well defined environment (i.e., non-adhesive synthetic hydrogel cone of defined geometry). These consistencies in the load and environmental test bed conditions enable precise quantitative comparisons to be made between cell types, as well as the quantification of the contributions of proteins or protein systems to the complex process of cell aggregation. An assay to quantify the collective forces that drive cell aggregation and the self-assembly of 3D microtissues can be employed (9). This assay measures the self-assembly of a multi-cellular toroid on a cone and it quantifies cell power, the work performed by the toroid as it moves up the nonadhesive cone against the force of gravity. Greater than about 50% of the power of a toroid could be reduced by blocking ROCK mediated contraction (9). The assay and cell power measurement to quantify the cell-cell mechanics that occur in mixes of two cell types in a 3D cellular environment are described.

The cell power assay described herein quantifies the work that cells do against the force of gravity as they self-assemble a toroid that ascends a cone shaped peg. The assay is used to quantify the power associated with the self-assembly of two cell types, normal human fibroblasts (NHF) and a rat hepatocyte cell line (H35), and to quantify the contribution of Rho kinase (ROCK) mediated cell contraction to the assembly of these cells. This invention measures power behind the assembly of mixed (NHF/H35) microtissues and examines the role of heterotypic adhesion in generating cell tension and creating a more active cell. The heterotypic environment is a very potent inducer of cell mediated tension and its contribution to cell power is significantly greater that of a very well known inducer of contractility transforming growth factor-$\beta$1 (TGF-$\beta$1). Further demonstrating the importance of heterotypic cell-cell interactions, heterotypic interactions were increased by changing the ratio of NHFs to H35s and/or by treating the NHFs with TGF-$\beta$1, cell power was substantially increased. Mathematical simulation of stress distribution shows that tensile forces can be enhanced and further propagated over longer distances due to this heterotypic interface. With relevance to wound healing and fibrosis, these data suggest that the initial heterotypic interactions between fibroblasts and parenchymal cells maybe more important than TGF-$\beta$1 in the activation of fibroblast and the generation of tension in tissue.

When small numbers of NHFs were mixed with H35s to form heterotypic toroids, there was a significant increase in cell power due solely to the heterotypic environment. NHF cell power in the heterotypic environment was five times greater than in the homotypic environment. By comparison, the cell power of NHF$^{TGF-\beta1}$ increased only two fold when compared to cell power for the NHF in the homotypic environment. The maximal increase in NHF cell power was cell ratio dependent. NHF cell power in the about 1:10 ratio was three times higher than the about 1:1 ratio. The about 1:10 ratio approximates the ideal about 1:12 ratio in close spheres packing, where one sphere contacts twelve nearest neighbors maximizing heterotypic cell interactions. Within the toroid, foci of heterotypic interactions were identified by staining for f-actin. NHFs were located at these foci of f-actin staining and the signal was significantly stronger than areas of the toroid where H35 homotypic interactions predominated. The f-actin staining at these heterotypic foci was not confined to just the NHF but extended into neighboring H35s suggesting that they were experiencing increased tension and had a reorganized cytoskeleton (17).

As the number of NHFs decreased, the time to reach peak power also decreased. For the 1:10 mix, power was undetectable for the first 4 hours and then rapidly rose to its peak power. One possibility is that this lag was necessary for NHFs to self-sort and form an inner toroid of NHFs within the heterotypic toroid. This was ruled out because these small numbers of NHFs are not able to form a contiguous toroid (9) and cell labeling showed that self-sorting did not coincide with peak power. Also, self-sorting of NHFs$^{TGF-\beta1}$ was reduced compared to untreated NHFs in the heterotypic environment. It is possible that the lag time is required for the changes to occur at the heterotypic interface that will result in increased power. NHFs may require time to sense and adapt to the increased load and/or make cytoskeletal changes at the heterotypic interface. Consistent with this possibility is the observation that after an hour of contact between a fibroblast and an epitheliocyte, the cortical actin of the epitheliocyte is disassembled and aligned with the radial actin of the adjacent fibroblast (22).

Although the cause of the increased power in the heterotypic environment is unclear, it is believed that the changes are due to the heterotypic interface between NHF and H35s. The modeling data suggests that when highly contractile fibroblasts are surrounded by non-contractile H35s there is a significant enhancement in stress for both the NHFs and in the adjacent H35s compared to that in the homotypic environment. The increase in tensile stresses can lead to actomyosin recruitment (23) and the strong foci of f-actin staining suggests that the heterotypic interface causes a reorganization of the actin cytoskeletons of the H35s surrounding NHFs. The H35 cortical actin that is now realigned would be part of a new contiguous hepato-fibro contractile unit with significantly more contractile force that could transmit stresses over greater distances. In this heterotypic contractile unit, both hepatocytes and fibroblast could make contributions to the enhanced power, perhaps via an increase in efficiency or recruitment of a power source that is only tapped through heterotypic interactions. Such a power source could be a more efficient and more effective arrangement of the cytoskeleton and the molecular motors that act on the cytoskeleton. Alternatively, a more optimal arrangement of membrane proteins that bind cells to one another could be the source or an optimal arrangement of cell membrane proteins and their connections to their respective cytoskeletons Whatever the mechanism, the time for these changes is fairly rapid since the peak power of the 1:10 toroid is manifest at 6 hours. Although NHFs and H35s could secrete growth factors known to activate contractility in the opposite cell type leading to increased power (24-26), as described herein, this is a minor contribution if at all because power did not significantly increase when the cells were seeded in conditioned media. As well, f-actin staining is specifically increased only at NHF/H35 interfaces and not H35/H35 interfaces in the same heterotypic toroid indicating that it is not soluble factors diffusing through the tissue to cause enhanced power.

Although the effect of the heterotypic environment was greater than TGF-β1 treatment, their combined effects were synergistic and resulted in a 22 fold increase in cell power when compared to NHFs. TGF-β1 is pleiotropic and its actions on fibroblasts grown on 2D substrates and embedded in 3D gels have been well defined (27-31). TGF-β1's ability to induce contractility of the fibroblasts is certainly one means by which power is increased in the homotypic and heterotypic environments. However, increased contractility alone does not explain the synergistic action of TGF-β1 treatment and the heterotypic environment. One possible explanation is that NHFs$^{TGF-β1}$ engage in more heterotypic interactions. This is supported by the observation that self-sorting of NHFs$^{TGF-β1}$ is reduced compared to untreated NHFs in the heterotypic environment. As self-sorting proceeds, NHFs segregate away from H35s and heterotypic interactions of higher power are exchanged with homotypic interactions of lower power. By inhibiting self-sorting, TGF-β1 treatment sustains the heterotypic interactions that lead to the most significant increase in power. This was evident in the 1:10 sample for which there was not a single, but two peaks in power.

The nature of the heterotypic interactions and how they give rise to increased power is unclear. Whereas, homotypic interactions of fibroblasts are well characterized and include the formation of large, stable cell-cell adherents junctions that transmit contractile stress (6) and cadherin expression that changes from N-cadherin to stronger OB cadherins (32). In addition to being mechanically coupled, fibroblasts engaged in homotypic interactions that are also electrochemically coupled via gap junctions (6). It remains to be determined how the heterotypic interface is coupled and how this coupling differs from the homotypic interface.

Change to the mechanical environment after tissue injury is an immediate and significant ongoing stimulus for scarring and fibrosis of numerous organs and tissues, including, but not limited to the liver. Soon after tissue injury, fibroblasts migrate out of the stable, stress shielding ECM and into a heterotypic environment where it interfaces for the first time with parenchymal cells, such as the hepatocyte, and the ratio of cell-cell interactions compared to cell-ECM interactions increase (6). The data described herein suggests that regardless of whether the fibroblasts are 22 times more powerful or the hepatocytes are as powerful as normal fibroblasts, the heterotypic interface is a stimulus significantly greater than TGF-β1 and that it may serve to increase contractility and/or be an initial event activating the fibroblast which in turn increases stress in the parenchyma, factors which could contribute to tissue fibrosis. The role of TGF-β1 role in this early stage is synergistic and would serve to sustain and increase these heterotypic interactions Inhibiting these very early events at the heterotypic interface may be a useful target for an anti-fibrotic strategy.

Methods and assays for forming microtissues and macrotissues, including spheroids, toroids and rods are described in U.S. Patent Application No: 2011/0212481, filed on Oct. 1, 2010, and entitled "Assays and Methods for Fusing Cell Aggregates to Form Proto-Tissues," by Morgan et al, the entire teachings of which are incorporated by reference in its entirety. Methods and devices for cell aggregation and encapsulation of cells are described in WO 2007/087402, having an international filing date of Jan. 24, 2007, and entitled "Cell Aggregation and Encapsulation Device and Method," by Morgan, et al. The entire teachings of which are incorporated by reference in its entirety.

The following examples are illustrative and not intended to be limiting in any way.

EXEMPLIFICATION

Example 1

Using planar substrates and collagen gels, the field of mechanotransduction has focused on the role of extracellular matrix stiffness, mechanical tension, and transforming growth factor-β1 (TGF-β1) in generating a more contractile fibroblast. However, little is known about the role of cell-cell interactions in inducing cellular contraction. A 3D self-assembled microtissues and a cell power assay (an assay for mechanotransduction) was employed to quantify the effects of TGF-β1 versus the heterotypic cell interface on the power exerted by pure normal human fibroblast (NHF), pure rat hepatocyte (H35) microtissues, and combinations of the cells. As a control, TGF-β1 only doubled the power output of pure NHF and pure H35 microtissues, whereas the heterotypic environment resulted in about a 5 fold increase in cell power (0.24±0.05 to 1.17±0.13 fJ/hr). Seeding TGF-β1 treated NHFs with untreated H35s demonstrated that the heterotypic environment and TGF-β1 synergistically increase cell power by 22× by maximizing heterotypic cell interactions. Using a mathematical simulation of stress generation, as described herein, tensile forces can be enhanced by heterotypic cell interactions, thereby providing a new understanding of how heterotypic cell interactions may increase cellular force generation during wound healing.

Materials and Methods

Micro-Mold Design and Gel Casting

Toroid molds suitable for side view microcopy were designed as previously described (9). Toroid molds were designed using the computer aided design (CAD) software Solid Works (Solid Works Corporation, Concord, Mass., USA). The mold was designed with 12 features to create wells. Each feature is a rounded edged (350 μm in diameter) cylinder (1.1 mm) with a cone indent in the center. The slope of the central cone was 65° and it is 650 μm in diameter. CAD files were used to produce thermowax molds with a rapid prototyping machine (3D Systems Corporation, Valencia, Calif.).

Wax molds were used to cast 13% polyacrylamide gels. Gels were removed from wax molds and transferred to six well culture plates. Each of the resulting wells is a circular trough confined by the hydrogel wall at the outer edge of the trough and by a conical peg on the inner edge of the trough. The gels were rinsed with fresh culture medium and then equilibrated overnight at 37° C. in 4 ml of DMEM supplemented with 1% penicillin/streptomycin (pen/strep). After equilibration, the medium was removed, and the gels were rinsed with fresh medium.

Cell Culture and Gel Seeding

NHFs (passage 4-10), derived from neonatal foreskins, and H35s (passage 5-11) were grown in T-175 flasks in DMEM with 10% FBS and 1% pen/strep at 37° C. and 10% $CO_2$. Cells were removed from flasks using a standard trypsin process. Briefly, cells were exposed to 0.05% trypsin for 10 minutes, quenched with serum containing medium, spun down at 800 rpm for 6 minutes, resuspended in a known volume of medium, and counted using a hemocytometer. Cell solution (70 μl) was added to each hydrogel. After 30 minutes, 4 ml of fresh medium was added to each of the wells. After seeding, images of the samples were taken every 2 hours for about 8 hours. Pure NHF microtissues were seeded with about 10,500, about 21,000, about 25,000 or about 35,000 cells/well. Heterotypic microtissues were seeded at ratios of about 1:1, about 2:3, about 1:4; about 1:6, about 1:10, about 1:16, and about 1:20 (NHF:H35). The seeding per well for heterotypic samples was kept constant at about 21,000 cells/well. For TGF-β1 experiments, NHFs and H35s were incubated for 48 hours in DMEM with 10% FBS, 1% penn/strep and 5 ng/ml human recombinant TGF-β1 (Invitrogen, Carlsbad, Calif., USA), passed according to standard protocol, and seeded at about 21,000 cells/well. NHFs$^{TGF-β1}$ coseeded with H35s were seeded in DMEM with 10% FBS, 1% penn/strep without additional TGF-β1.

For sorting experiments, NHFs and H35s were incubated with 2.5 μM CellTracker™ Red CMPTX and CellTracker™ Green CMFDA™ (Invitrogen, Carlsbad, Calif., USA), respectively, in serum free media for 30 minutes. After incubation, the dye was aspirated and the cells equilibrated in serum media for 1 hour prior to passing. For NHF$^{TGF-β1}$:H35 sorting experiments NHFs were incubated for 48 hours in DMEM with 10% FBS, 1% penn/strep and 5 ng/ml TGF-β1. After incubation the NHF$^{TGF-β1}$ and H35s were fluorescently labeled and passed as previously described.

To investigate the effect of paracrine factors, media from homotypic toroids containing about 10,500 H35s and from homotypic toroids containing about 10,500 NHFs was collected. The conditioned media was seeded about 10,500 NHFs with the media collected from the H35s and also seeded about 10,500 H35s with the media collected from the NHFs. Power was analyzed at four hours since this is the time enhanced power for heterotypic toroids which contained about 10,500 H35s and about 10,500 NHFs (1:1 samples).

To determine if extracellular calcium disintegrated the microtissues, 1:1 (NHF: H35) microtissues were cultured for 4 hours. Culture media was removed, and microtissues were washed with PBS, and then incubated overnight at 37° C. in 5 mM EDTA in PBS. Control samples were kept in regular culture media or PBS.

Microscopy and Image Analysis

Convential view fluorescent and phase images were captured using Carl Zeiss Axio Observer Z1 with an AxioCam Mrm camera (Carl Zeiss MicroImaging, Thornwood, N.Y., USA). To capture side view images, a Mitutoyo FS-110 microscope was modified to lie on its back and a translational stage was added to hold samples. Samples were imaged in bright field through the eyepiece of the microscope. ImageJ Software (NIH Rasband, W.S. USA) was used to measure the height of the toroid, the major radius, and the minor radius of the toroid.

Immunohistochemistry and Confocal Microscopy

Prior to passing, NHFs were incubated with CellTracker™ Red CMPTX in serum free DMEM for 30 minutes. Fluorescently labeled NHFs were seeded with unlabeled H35s. Eight hours post-seeding, microtissues were fixed overnight in 4% paraformaldehyde. Samples were then rinsed 3 times with 0.002% Triton X-100 and permeabilized for 6 hours in 0.5% Triton X-100. Microtissues were then incubated with 1 ml of 300 nM DAPI dihydrochloride and Oregon Green 488 Phalloidin (Invitrogen, Carlsbad, Calif., USA) for 1 hour. Confocal images were captured with a Zeiss LSM 510 confocal microscope (Carl Zeiss MicroImaging, Thornwood, N.Y., USA).

Principle Stress Modeling

To model the tensile stresses generated by the contractility of the NHFs in homotypic and heterotypic environments, finite element simulations were conducted by assuming linear elastic constitutive relations (Young's modulus E=2 kPa and Poission's ratio=0.5 (5)) for both the NHFs and H35s. The stresses in the toroids were computed in the finite element framework using the package ABAQUS v6.10 (SIMULIA, Providence, R.I., USA). Since there are no constraints along the z-direction and as the thicknesses of cell aggregates are smaller than their lateral dimensions in the x-y plane, plane stress elements CPS3 were used in all the finite element simulations. The peg was assumed to be rigid and the contact between the peg and the cells were modeled using normal hard-contact elements.

From a mechanistic perspective, the deformation and stresses created in an actin network by myosin motors can be modeled by treating the motors as force dipoles (10-13). This is because the motors exert equal but opposite forces along the actin filaments. When a large number of these motors are involved as in the case of cell aggregates, a coarse-grained description based on contractile strain, which gives the measure of the dipole strength per unit volume can be adopted. Mathematically, the elastic fields arising from the contractile strain due to myosin motors is similar to the fields created by sources of internal stress in solid materials, for example temperature fields, where thermal strain leads to the body forces (14). In the simulations, thermal strain induced by the spatially varying temperature fields, implemented in ABAQUS v6.10, is used to model the contractility in the cell aggregates. In all the simulations, the contractile strain in NHFs is assumed to be uniform and isotropic (magnitude=0.01), while the contractile strain in the H35s is assumed to be negligible. To investigate the effect of shape and stiffness of the cells on the enhancement of stresses in heterotypic mixes, the changes in stress with NHF aspect ratios of 2 and 5 (major/minor radius) and H35 stiffness increased 5 fold were considered.

Results

The range of power exerted by increasing numbers of NHFs (>3 fold) in a homotypic environment by seeding the cells into non-adhesive hydrogels with toroid recesses, each with a central cone (65° slope) was measured. Cells settled and formed cell-cell adhesions that drove the toroid shaped microtissue up the cone. The power necessary to move the NHF toroid up the cone as P=ΔW/Δt was calculated, where ΔW is work performed against gravity to move a toroid of a known mass to a given height, and Δt is the time over which the work is performed (9). NHF toroid height (FIGS. 2A-2D) did not change with increasing NHF cell number (186±19 μm, 2 hrs). Toroid power increased linearly as cell number increased, but power per NHF (cell power) was independent of cell number, with a peak cell power of 0.22±0.02 fJ/hr (2 hrs) and an average cell power (over all time points) of 0.16±0.03 fJ/hr.

Figure 3:
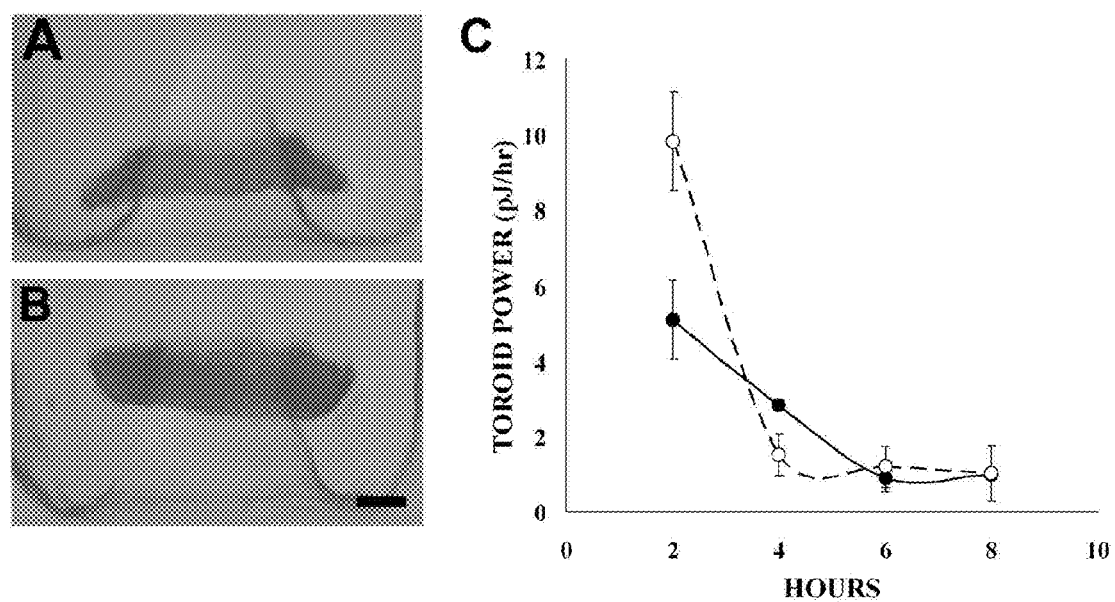
FIGS. 3A-3C: TGF-β1 treatment increased NHF power. NHFs were treated for 48 hours in 5 ng/ml TGF-β1 and then seeded into toroid recess. After 2 hours, toroids of NHFs treated with TGF-β1 (B) moved twice as far up the peg compared to untreated NHFs (A). (C) TGF-β1 treatment (open circles) resulted in doubling in cell power (p<0.05) relative to the untreated controls (closed circles). n=8 for both groups. Scale bar is 200 μm.
Figure 4:
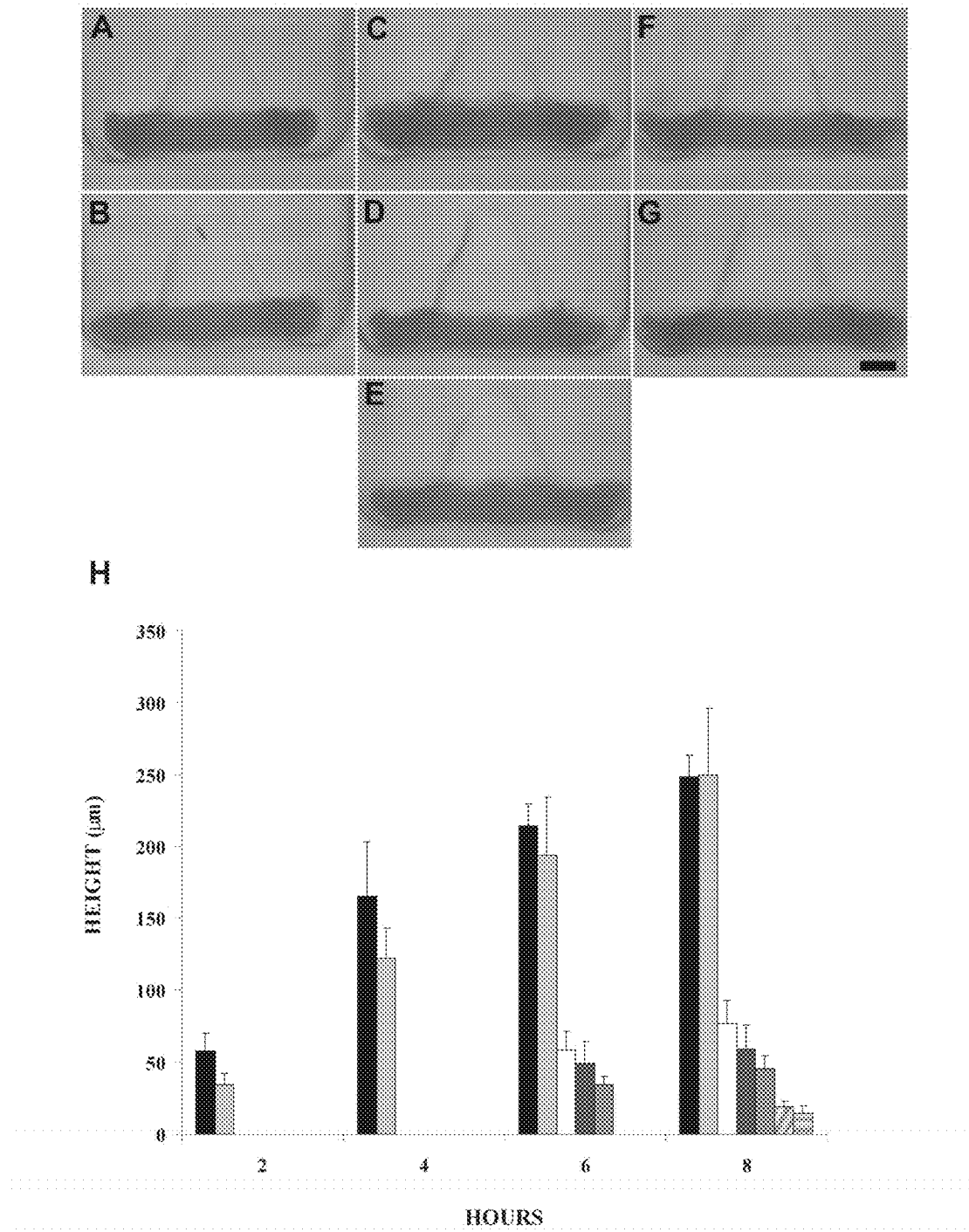
FIGS. 4A-4H: Heterotypic mixtures of NHFs and H35s self-assemble into toroids and move up the conical pegs at different rates. 1:1 (A) and 2:3 (B) samples after 2 hours 1:4 (C), 1:6 (D), and 1:10 (E) samples after 6 hours and 1:16 (F) and 1:20 (G) samples after 8 hours. Toroid height (H) increased over time and decreased as ratio of NHFs to H35s decreased for the 1:1 (■), 2:3 ( ) 1:4 (□), 1:6 (■), 1:10 ( ), 1:16 (diagonal stripes), and 1:20 (horizontal stripes) samples. Scale bar is 200 μm.

To understand TGF-β1's effects on power, NHFs were treated with TGF-β1 and seeded into the toroid recesses. As early as two hours, height of the NHF$^{TGF-β1}$ toroid increased two fold resulting in a significant increase in toroid power (9.82±1.32 pJ/hr versus 5.08±1.04 pJ/hr for controls) (FIGS. 3A-3C). Peak cell power (2 hrs) for NHF$^{TGF-β1}$ was 0.47 fJ/hr (2 hrs) and average cell power was 0.16±0.21 fJ/hr. TGF-β1 also increased the power of homotypic toroids of H35s, a rat hepatocyte cell line. Untreated H35 toroids required 48 hours to move the same distance that NHF toroids moved in two hours (9). TGF-β1's effects on H35s were evident at 24 hours. H35$^{TGF-β1}$ toroid and cell power both doubled to 0.45±0.08 pJ/hr and 0.022±0.004 fJ/hr, respectively, compared to untreated controls.

To examine cell power in a heterotypic environment, mixtures of NHFs and H35s were seeded with the total number of cells per toroid held constant (~21,000). Heterotypic toroids moved at different rates and reached different heights (FIGS. 4A-4H). Power of the heterotypic toroids decreased as the percentage of NHFs decreased and there was a delay to reach peak toroid power (FIGS. 4A-4H). To determine the effect of the heterotypic environment in conjunction to TGF-β1 treatment, $NHF^{TGF-\beta1}$ were mixed with untreated H35s at varying ratios. All treated heterotypic toroids moved further up the peg with the 1:1, 1:10, and 1:20 samples moving 1.4, 4.4, and 6.3 times higher than their respective controls.

Interestingly, when NHFs or $NHFs^{TGF-\beta1}$ where seeded with H35s there was enhanced power. To make quantitative comparisons of the enhancement in cell power due to the heterotypic environment, we calculated the projected power of a toroid and compared it to its actual measured power to derive a value for enhanced toroid power (Table 1).

TABLE 1

| Heterotypic Toroids | Measured Toroid Power (pJ/hr) | Projected Toroid Power (pJ/hr) | Enhanced Toroid Power (pJ/hr) | NHF has Enhanced Power (fJ/hr per NHF) | Relative Increase in NHF Cell Power | H35 has Enhanced Power (fJ/hr per H35) |
|---|---|---|---|---|---|---|
| 1:1 (NHF:H35) | 4.02 | 2.50 | 1.52 | 0.39 | 1.6x | 0.15 |
| 1:10 (NHF:H35) | 2.21 | 0.45 | 1.75 | 1.17 | 4.9x | 0.09 |
| 1:20 (NHF:H35) | 1.01 | 0.24 | 0.77 | 1.02 | 4.2x | 0.04 |
| 1:1 ($NHF^{TGF-\beta}$:H35) | 6.05 | 4.90 | 1.16 | 0.58 | 2.4x | 0.11 |
| 1:10 ($NHF^{TGF-\beta}$:H35) | 5.30 | 0.89 | 4.41 | 5.30 | 22.1x | 0.23 |
| 1:20 ($NHF^{TGF-\beta}$:H35) | 4.10 | 0.47 | 3.63 | 4.13 | 17.2x | 0.18 |

The data shown in Table 1 show heterotypic toroids have enhanced power. Measured toroid power was the toroid power exhibited at the time of peak power for each of the samples (about 1:10 is the combination of 6 and 8 hours as there were two peaks in power). Projected toroid power equals the power per NHF (homotypic toroid) or TGF-β treated NHF multiplied by the number of NHFs in the mixed toroid. Enhanced toroid power equals the difference between the measured toroid power and the projected toroid power. When treated with TGF-β and in the heterotypic environment NHFs are 22× more powerful if enhanced power is distributed to NHFs. If enhanced power is distributed to the H35, the H35 has enhanced power in the range of untreated NHFs.

For each mixture, since the power of a homotypic H35 toroid is undetectable in 8 hours, projected toroid power was calculated from the number of NHFs present in the mix multiplied by cell power value as measured in the corresponding homotypic environment (NHF or $NHF^{TGF-\beta1}$). The enhanced toroid power can be attributed to the increased activity of one of the two cell types in the mix (NHF or H35) or it can be attributed to the heterotypic interface where both cell types interact. Since the homotypic H35 toroid power is undetectable at eight hours, we first looked at the resulting NHF cell power as if NHFs are the sole power generator in the system. This is an upper bound to just how powerful the NHF could become. Surprisingly, NHF cell power increased as the percentage of NHFs decreased, with the about 1:10 ratio exerting the greatest peak power per NHF (1.17±0.13 fJ/hr). This NHF cell power value in the heterotypic environment was 5 times greater than NHF cell power in the homotypic environment (100% NHFs; 0.24 fJ/hr), and about 2.5 times greater than the effect of TGF-β1 treatment.

Figure 5:
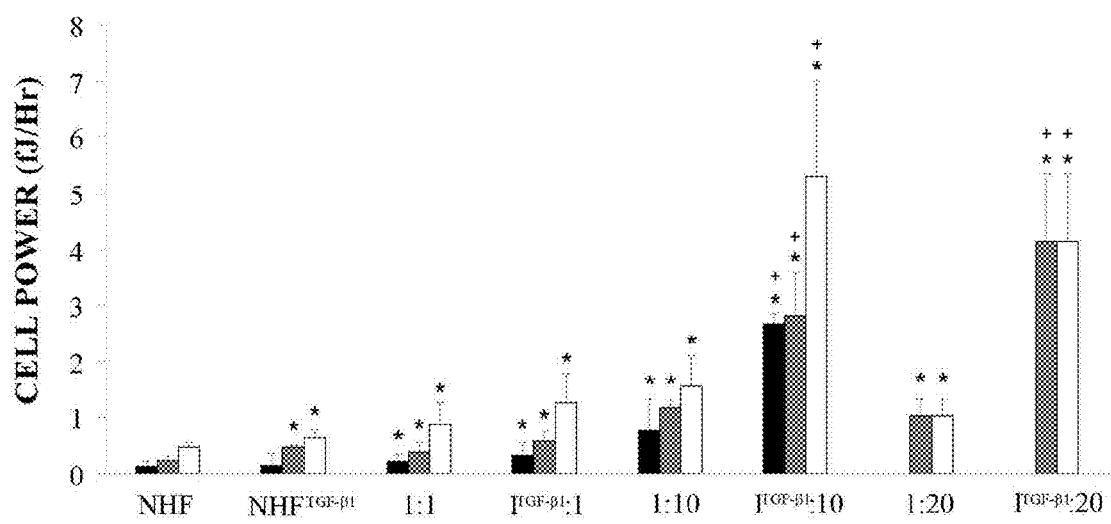
FIG. 5: NHF Cell power increased with TGF-β1 and the heterotypic environment. Average cell power (black bars), peak cell power (gray bars) and total cell power (white bars) were calculated for each sample with the assumption that all power is generated by the NHFs. Average cell power was calculated as the mean power per cell value for each sample (over the time in which the samples exerted power), peak cell power is the maximum cell power output of each sample at a single time point, and total cell power is the sum of the cell power over the duration of the experiment. * indicates significant differences in sample when compared to homotypic NHF+ indicates significant difference when treated with TGF-131 than untreated controls. n≥6 for all groups.

Likewise, $NHF^{TGF-\beta1}$ cell power increased in the heterotypic environment as the percentage of $NHF^{TGF-\beta1}$ decreased with the about 1:20 mix exerting the greatest peak cell power (4.13±1.22 fJ/hr) and the about 1:10 mix exerting the greatest total cell power of 5.3±1.32 fJ/hr between four and eight hours (FIG. 5) meaning that the cell power of the $NHF^{TGF-\beta1}$ is increased by greater than about 11 times in the heterotypic environment. When compared to untreated NHFs in a homotypic toroid, TGF-β1 treatment in conjunction with the heterotypic environment causes cell power to increase by greater than about 22 times. Since TGF-β1 alone only doubles cell power, and the heterotypic environment alone only increases power 5 fold, the combination of these two factors is synergistic.

Alternatively, if the enhanced toroid power is attributed solely to the H35 and is distributed among all H35s in the toroid, the power per H35 is increased from near zero (homotypic environment) up to 0.23 fJ/hr (about 1:10 mix). This enhanced cell power value for an H35 is very large considering that baseline H35 cell power in a homotypic toroid is very small (0.022 fJ/hr, detectable 24 hours post seeding) (9), and that such an enhanced value would be in the range of untreated NHFs in a pure NHF toroid.

Figure 6:
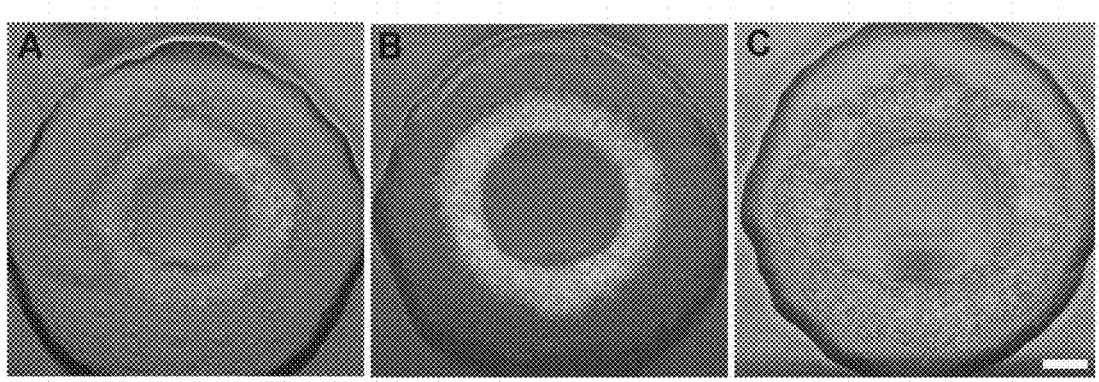
FIGS. 6A-6C: NHFs self-sort with H35s within 4 hours for ratios greater than 1:4. NHFs (red) were seeded with H35s (green) and self-sorting was evaluated. For the 1:1 (A) and the 2:3 (B) ratios (NHF:H35) sorting was present at four hours. However, when the ratio was greater than 1:4 (C) self-sorting was to a lesser extent or absent. Scale bar us 200 μm.
Figure 7:
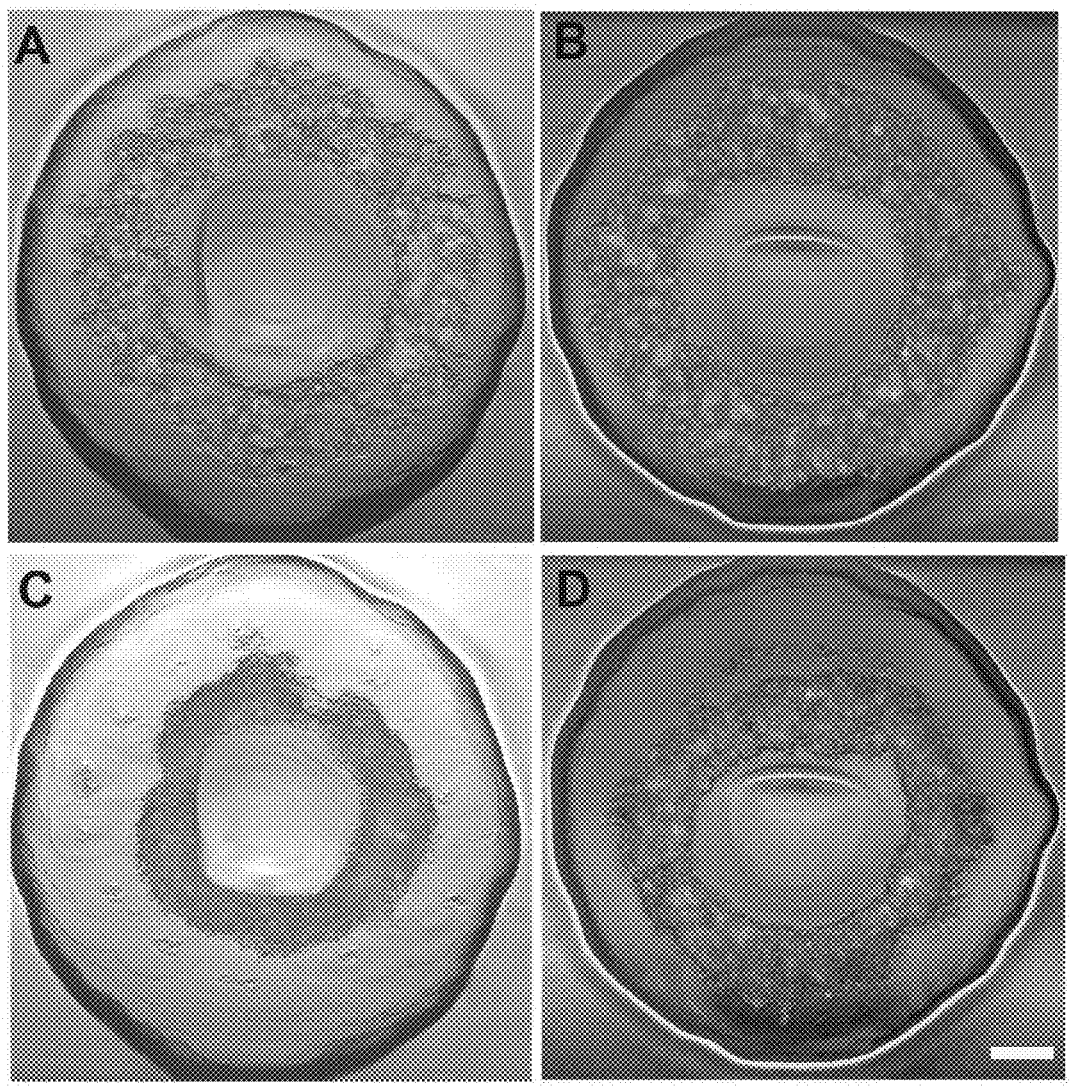
FIGS. 7A-7D: Delay in peak power was not related to the time to self-sort and TGF-β1 treatment decreased sorting. NHF/NHF$^{TG-β1}$ (red) and H35s (green) were seeded at a 1:10 ratio. For untreated samples (A and C), sorting is visible at 24 hours (C) with NHFs (red) taking the interior position and H35s (green) the exterior; but, sorting was absent in the peak power time (A). TGF-β1 treatment of NHFs prevented sorting (B and D) as sorting was absent at both the peak power time (B) and 24 hour time point (D). Scale bar is 200 μm.
Figure 8:
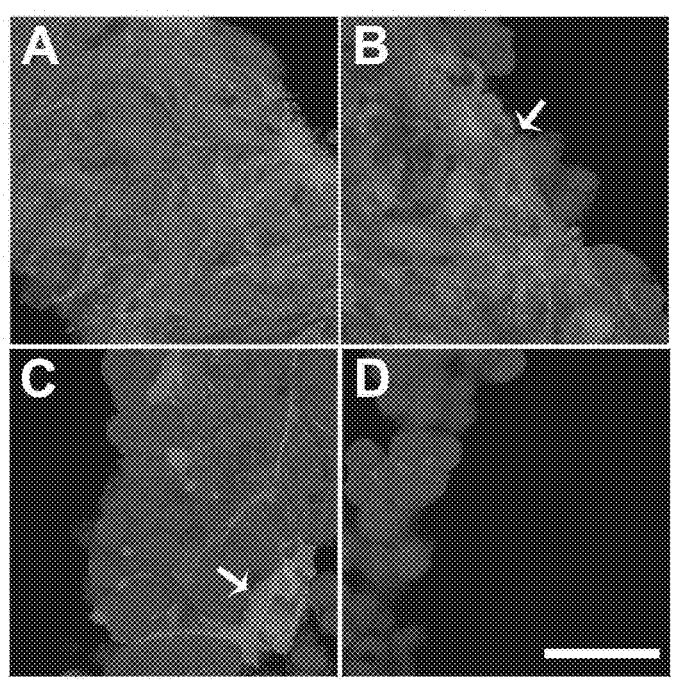
FIGS. 8A-8D: Cytoskeletal architecture was altered in the heterotypic environment. Pure NHF (A), 1:1 (B), 1:10 (C), and pure H35 (D) microtissues were fixed and stained after 8 hours. The nuclei and f-actin of all cells was labeled with DAPI™ (blue) and phalloidin (green), respectively and NHFs were labeled with CellTracker™ Red prior to self-assembly. H35s are identified as cells with a blue nuclei without red staining. Pure NHF microtissues had a dense, continuous f-actin network while pure H35 microtissues had a week punctuate f-actin signal. In heterotypic mixes, there was an enhanced f-actin signal at the junction between NHFs and H35s which met the nuclei of the H35. The arrow indicates the area in which the f-actin signal was enhanced due to the heterotypic interface. The f-actin signal was only seen at the interface of the hepatocyte and the fibroblast. Scale bar is 50 μm.

For each of the mixes, there was a delay in toroid motion before peak power was reached. For homotypic NHF toroids, peak power was reached at the first time point (2 hours). As the percentage of NHFs in the mixes decreased, the time to reach peak power increased. To determine if this delay was due to the time for cells to self-sort, NHFs and H35s were fluorescently labeled and sorting was assessed (FIGS. 6A-6C). When the proportion of NHFs was high, the cells self-sorted within eight hours with NHFs forming a contiguous inner toroid with a circumferential coating of H35s. When the percentage of NHFs was reduced (<1:4), the NHFs no longer sorted within the eight hours, nor formed a contiguous inner toroid, but were distributed throughout the toroid. In the 1:10 mix, sorting was evident after 24 hours, with the NHFs clustering into pockets centrally located in the toroid. Interestingly, this sorting was eliminated by treating the NHFs with TGF-β1 (FIGS. 7A-7D). Thus, neither sorting nor the formation of a contiguous NHF toroid is necessary (or the mechanism) for the movement of the toroid at low percentages of NHFs and TGF-β1 treatment inhibits self-sorting.

To examine if enhanced power was transduced through cell-cell interactions 1:1 (NHF:H35) were cultured for four hours and then incubated in EDTA to destabilize the calcium dependent cell-cell adhesions. Control samples were kept in regular culture media or PBS. Microtissues incubated in EDTA disintegrated into monodispersed cells whereas control samples in both media and PBS maintained their integrity indicating that cell-cell junctions are needed for mechanotransduction.

To determine if enhanced power was due to paracrine factors secreted by NHFs and/or H35s, the media from homotypic toroids containing about 10,500 H35s and from homotypic toroids containing about 10,500 NHFs was collected. This conditioned media was seeded with about 10,500 NHFs with the media collected from the H35s and also seeded about 10,500 H35s with the media collected from the NHFs. Power was analyzed at four hours since this is the time when the heterotypic samples which contained about 10,500 H35 and about 10,500 NHFs (1:1 samples) had enhanced power. Similar to control H35 microtissues, H35s seeded in NHF conditioned media had no power. For NHF microtissues seeded in H35 conditioned media there was no enhancement in power as compared to controls (p=0.6). Specifically, the power for control NHF microtissues was 0.19±0.06 fJ/hr per cell and power for NHF microtissues in conditioned media was 0.18±0.03 µJ/hr per cell.

To investigate cytoskeletal changes in the heterotypic environment, toroids were stained for f-actin. Confocal images revealed that the gross cytoskeletal architecture were very different for homotypic versus heterotypic toroids (FIGS. 8A-8D). The arrow indicates the area in which the f-actin signal was enhanced due to the heterotypic interface. The f-actin signal was only seen at the interface of the hepatocyte and the fibroblast. Homotypic NHF toroids had a continuous and dense f-actin network spanning the thickness of the toroid, whereas homotypic H35 toroids had weak punctuate f-actin staining only at cell junctions. Heterotypic toroids (1:1 and 1:4) exhibited a dense f-actin network throughout the central NHF portion of the toroid up to the H35 junction. The 1:10 mix had dense f-actin networks focused around the NHFs that was randomly distributed through the thickness of the toroid, as NHFs had not yet sorted to the center.

Figure 9:
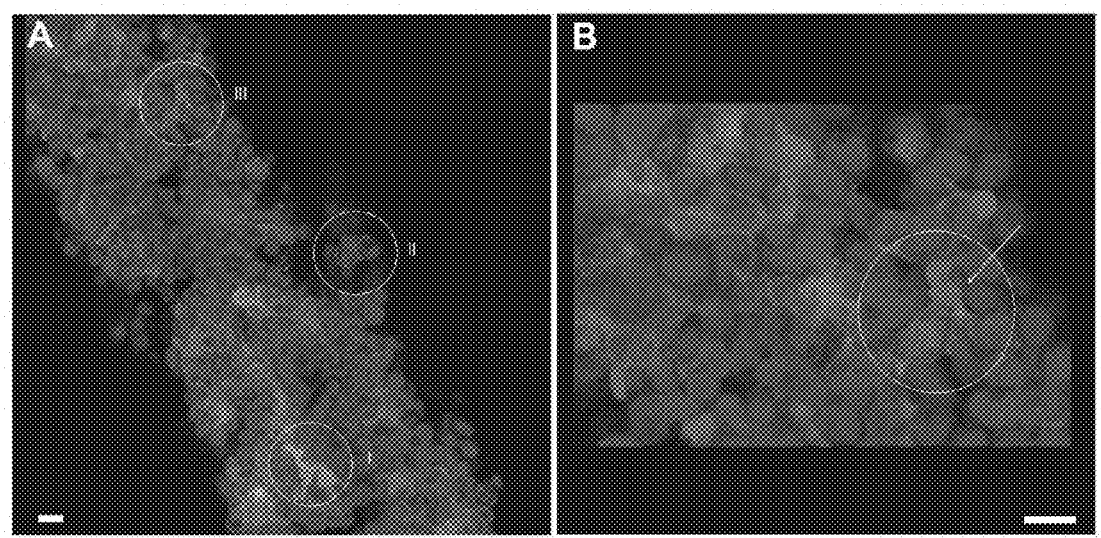
FIGS. 9A and 9B: f-actin signal is strong in areas where H35s contact NHFs. Heterotypic toroids (1:10) were fixed at 8 hours and nuclei stained with DAPI (blue) and f-actin with phalloidin (green). NHFs were labeled with Cell Tracker Red™ prior to self-assembly and H35s are identified as cells with blue nuclei but without the red stain (A, B). F-actin staining was strong in areas with high concentrations of NHFs (I). Areas of H35s, not in contact with NHFs, had a weak f-actin signal (II). H35s in contact with NHFs have a distinctly strong f-actin signal (III). (b) Higher magnification of region (III) shows a strong f-actin signal located at the junction of an NHF and surrounding H35s. The f-actin signal continues to the nuclei of H35 cells. The arrow indicates the area in which the f-actin signal was enhanced due to the heterotypic interface. The f-actin signal was only seen at the interface of the hepatocyte and the fibroblast. Scale bar is 20 μm.

H35s in direct contact with NHFs had a stronger f-actin signal than both H35s that were not in contact with NHFs and than H35s in a homotypic toroid. In the 1:20 mix, there were three different local cellular environments with distinct f-actin staining (FIGS. 9A and 9B). The arrow indicates the area in which the f-actin signal was enhanced due to the heterotypic interface. The f-actin signal was only seen at the interface of the hepatocyte and the fibroblast. One region had a high density of NHFs (I) with an f-actin network similar to that of a homotypic NHF toroid. Another region had a high density of H35s distant from NHFs (II) and an f-actin network similar to that of a homotypic H35 toroid. A third region had a single NHF surrounding a cluster of H35s (III) with a distinct cytoskeletal structure at the NHF/H35 interface; a strong f-actin signal extending from the NHF to the nuclei of the surrounding H35s.

Figure 10:
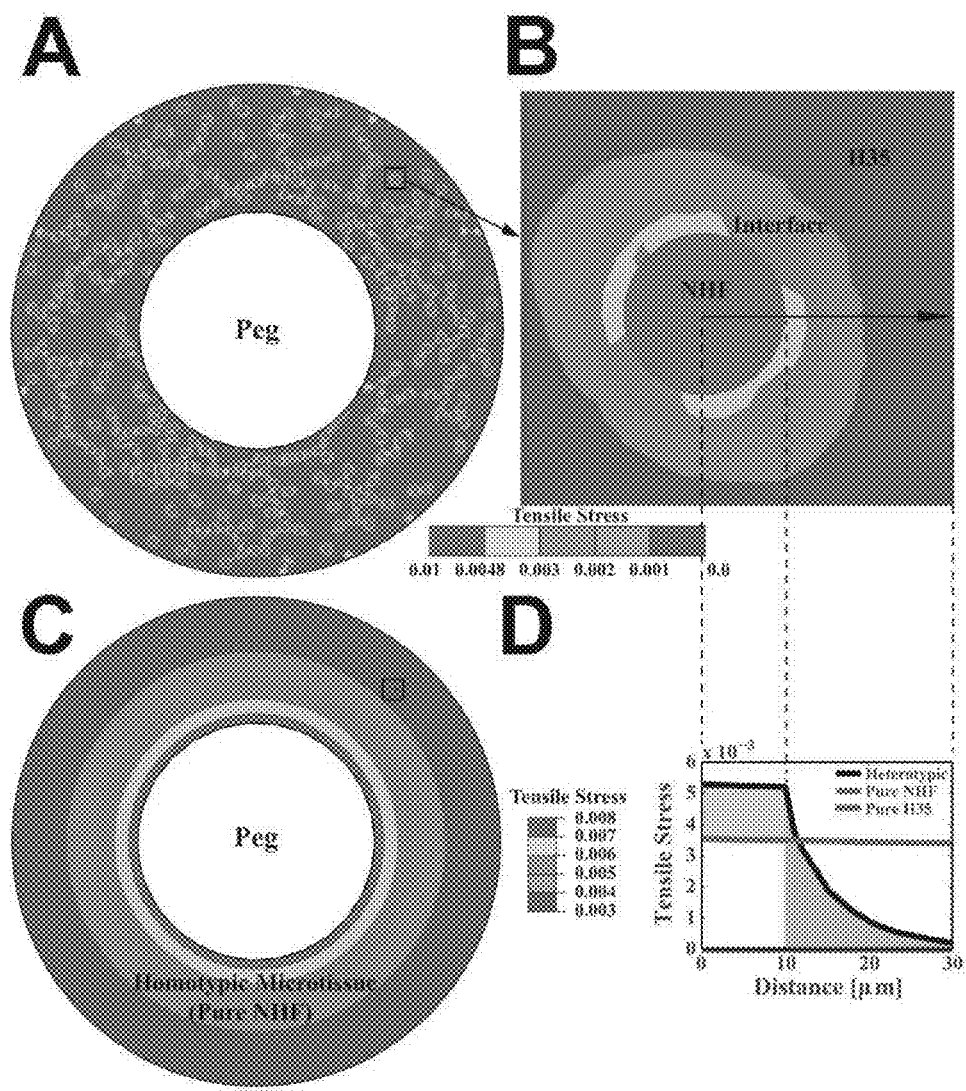
Figure 11:
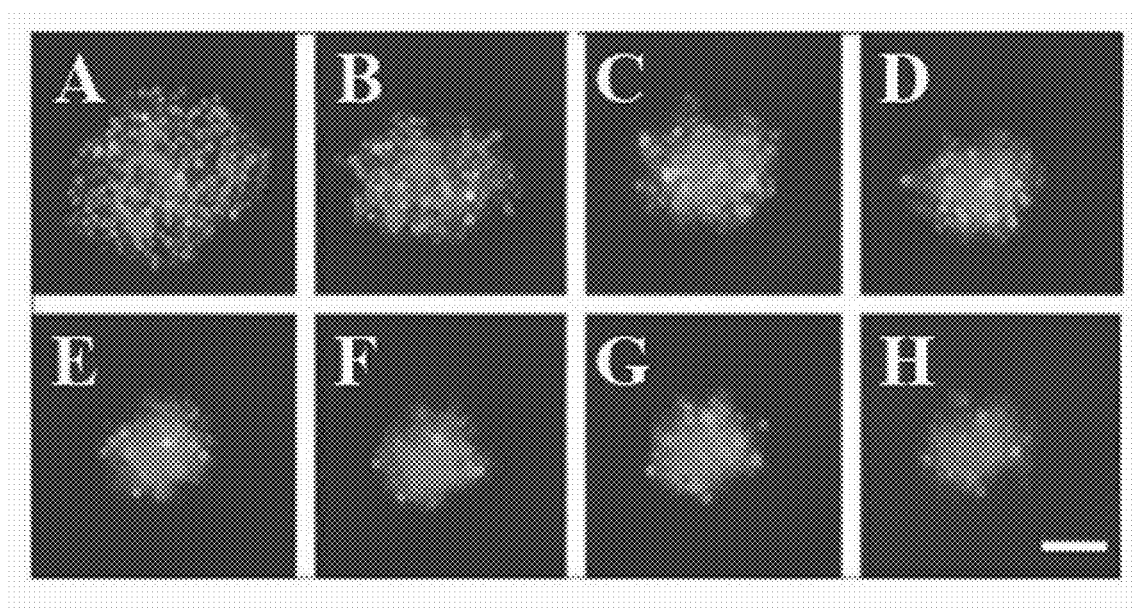

Tensile stress modeling demonstrated that the heterotypic environment increases stresses. In homotypic NHFs, the peg constrains the tissue from contracting leading to tensile stresses that decrease in magnitude radially outward from the surface of the peg (FIGS. 10A-10C). For the heterotypic tissue, in addition to the constraints from the peg, there is a new and more significant mechanism generating tensile stresses. Since the H35s that surround the NHFs are less contractile, they act as a resistance to the NHFs that are trying to contract. This generates tensile stresses both in the NHFs and the H35s (refer to FIG. 10B). The tensile stresses decrease from the NHF boundary to the surrounding H35s. The tension in both the NHF and the adjacent H35s is significantly higher than the corresponding tension in the respective homotypic environments.

Enhancement of mechanical tension also induces actomyosin activity in both cell types which would increase overall power in the heterotypic environment. This is consistent with the f-actin distribution which shows that the cortical actin of the H35 is rearranged and more aligned with the radial actin of the adjacent NHFs. Changes in tensile stresses in a heterotypic environment can be further enhanced for both the NHF and H35 by considering factors such as the shape of the NHF and differences in elastic stiffness of the cell types (Table 2).

TABLE 2

| NHFs' shapes | Average tensile stress in the NHFs | Stress at center of the surrounding H35s | Stress enhancement in the NHFs |
|---|---|---|---|
| Round | 0.0053 | 0.0019 | 1.5X |
| Ellipse (a/b = 2) | 0.0069 | 0.0012 | 2.0X |
| Ellipse (a/b = 5) | 0.0084 | 0.0009 | 2.4X |
| Ellipse (a/b = 5) with the different stiffness 5:1 (H35:NHF) | 0.0125 | 0.0042 | 3.6X |

The shapes of NHFs and the differences in the elastic moduli of the two cell types determine the enhancement of stress in heterotypic mixes as shown in Table 2. The elliptic shapes are characterized by the ratio of the major axis (a) to the minor axis (b). All the stresses are normalized by the Young's modulus of NHFs (2 kPa). Stress enhancement equals the ratio of stresses in heterotypic environments to the stresses (0.0035) in homotypic NHFs located close to the periphery of the torus.

Modeling the NHF as an elongated ellipsoid (aspect ratio=5) doubles the tensile stress and if the stiffness of the H35s surrounding the NHFs is larger by a factor of 5, than the tensile stress is increased by four fold. For a given level of contractile strain in the NHF, the tensile stress generated in the heterotypic environment will depend on the shape of the NHFs. For an elliptic shape, the largest (tensile) principal component of stress in the NHF increases with increasing aspect ratio compared to the principal stresses in a circular shape. Since an increase in tensile stresses lead to an increase in contractility, our calculations shows that an enhancement in power can be expected in more elongated NHFs.

Example 2

Using Cell Power to Identify Drugs

Using our toroid-on-cone assay, we quantified the power of normal human fibroblasts (NHFs) and compared this to heterotypic toroids (NHF: H35 mixtures) where we reduced the proportion of NHFs (50%, 10%, 5%). In all cases, total cell number in the toroid was held constant (about 21,000). The effects of TGF-β1 treatment were quantified. We used the values of toroid power to calculate cell power based on the number of cell in the toroid (Table 3). As the proportion of NHFs was decreased, the power of the entire toroid decreased as would be expected. During the measurement time for homotypic NHF toroids or heterotypic torioids, homotypic toroids with 100% H35 showed no movement and no power in this time interval. Homotypic H35 toroids require 48 hours to move the same distance as homotypic NHF toroids. Thus, the majority of the power of the heterotypic toroids can be credited to the NHFs in the mix. Power per NHF (NHF cell power) was calculated. NHF cell power in the heterotypic environment was increased about 4.9 fold compared to NHF cell power in the homotypic environment. When treated with TGF-[3]. NHF cell power in the homotypic environment was increased about 1.9 fold. Surprisingly the heterotypic environment had more of an effect on NHF cell power that TGF-β1 treatment (4.9 fold vs. 1.9 fold). When both were combined (TGF-β1 treated NHFs in the heterotypic environment) the effects were synergistic and NHF cell power was increased about 22.1 fold (10% NHFs: 90% H35s). Cell-to-cell generated biomechanics is the driving force for the movement of the toroid up the cone. The power analysis quantifies these driving forces and enables us to make quantitative comparisons of the effects of the heterotypic environment versus the effects of TGF-β1 treatment.

TABLE 3

Heterotypic cell interactions enhance NHF cell power more than TGF-β.

| | Toroid Power (pJ/hr) | Enhancement in Toroid Power (pJ/hr) | Enhancement in NHF Cell Power (fJ/hr/NHF) | Fold Increase in NHF Cell Power | |
|---|---|---|---|---|---|
| HOMOTYPIC TOROIDS | | | | | |
| 100% H35s | 0.26 | | | | |
| 100% NHF | 5.10 | | | | |
| 100% H35$^{TGF\text{-}\beta}$ | 0.45 | 0.19 | | | |
| 100% NHF$^{TGF\text{-}\beta}$ | 9.80 | 4.7 | 0.23 | 1.9x | Effects of TGF-β alone |
| HETEROTYPIC TOROIDS | | | | | |
| 50%:50% (NHF:H35) | 4.02 | 1.52 | 0.39 | 1.6x | |
| 10%:90% (NHF:H35) | 2.21 | 1.75 | 1.17 | 4.9x | Effects of heterotypic environment alone |
| 5%:95% (NHF:H35) | 1.01 | 0.77 | 1.02 | 4.2x | |
| 50%:50% (NHF$^{TGF\text{-}\beta}$:H35) | 6.05 | 1.16 | 0.58 | 2.4x | |
| 10%:90% (NHF$^{TGF\text{-}\beta}$:H35) | 5.30 | 4.41 | 5.30 | 22.1x | Effects of TGF-β & hetero environment |
| 5%:95% (NHF$^{TGF\text{-}\beta}$:H35) | 4.10 | 3.63 | 4.13 | 17.2x | |

Power of homotypic and heterotypic toroids were measured (toroid power). Total enhancement in toroid power (pJ/hr) versus control due to TGF-β treatment, the heterotypic environment or both was calculated. Since NHFs supply the vast majority of power, the increase in NHF cell power (fJ/hr) was calculated based on the number of NHFs in each toroid. The resulting fold increase in NHF cell power due to TGF-β treatment, the heterotypic environment or both was calculated. The effects of TGF-β treatment alone are only a about 1.9 fold increase in NHF cell power, whereas the heterotypic environment increased NHF cell power by about 4.9 fold. When TGF-β treatment was combined with the heterotypic cell environment the effects were synergistic and resulted in about 22.1 fold increase in NHF cell power.

Figure 12:
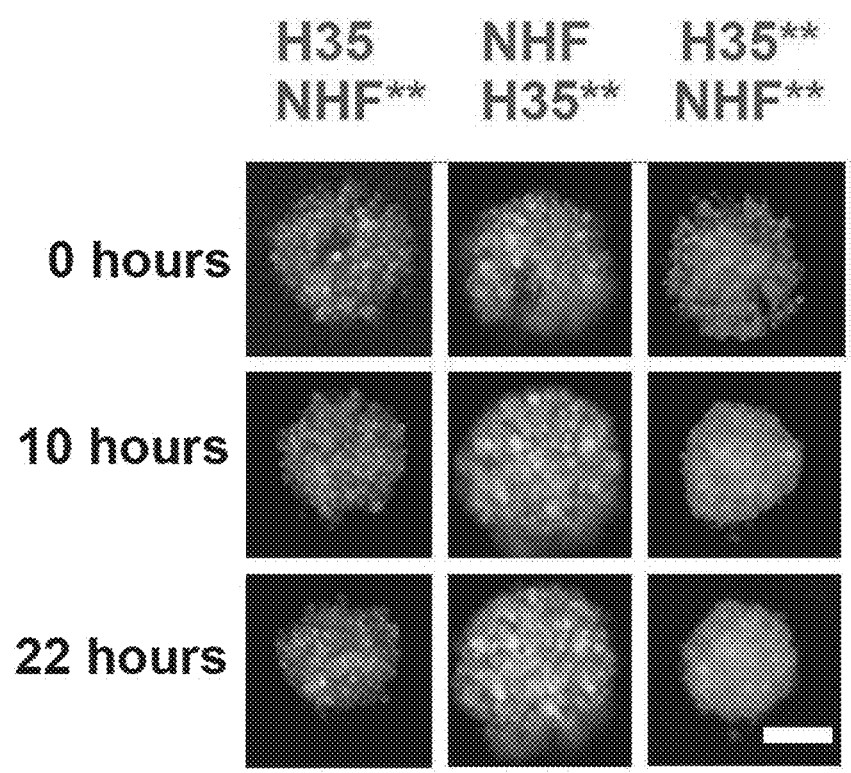
FIG. 12: Fluorescent images at different time points were taken of mixes (1:1) of NHFs and H35s that were treated with TGF-β1 (**) or untreated. Cells labeled red or green as indicated by color of label.

Using self sorting to identify drugs, TGF-β1 is a growth factor linked to fibrosis and well known for its ability to increase cell mediated contraction and synthesis of extracellular matrix proteins such as collagen. Using the invention, we show that TGF-β1 increases mechanotransduction by increasing the heterotypic interface between two different cell types. TGF-β1 increases this heterotypic interface by inhibiting the self-sorting that occurs when two different cell types self-sort as the self-assemble a spheroid. A mixture of NHFs and H35s will self-sort (NHF core, H35s outer coating)) FIG. 11A-11H. The NHFs are fluorescently labeled red and the H35s are fluorescently labeled green. As self-sorting proceeds, the NHFs form the inner core and the H35s form the outer coating. Also, as self-sorting proceeds the quantity of heterotypic interface decreases and the homotypic interface increases as cells partition. When we used our invention to determine TGF-β1's effects on self-sorting, we found that it inhibited self-sorting (FIG. 12). Thus, by inhibiting self-sorting, TGF-β1 treatment decreases the homotypic interface thereby increasing the heterotypic interface; the same heterotypic interface that increase NHF cell power. This shows that TGF-β1 mediates its action by increasing the heterotypic interface. Thus, the increase in the heterotypic interface drives the increase in cell power.

REFERENCES

1. Chen, C. S., Tan, J., and Tien, J. (2004) Mechanotransduction at cell-matrix and cell-cell contacts, *Annu Rev Biomed Eng* 6, 275-302.
2. Makrilia, N., Kollias, A., Manolopoulos, L., and Syrigos, K. (2009) Cell adhesion molecules: role and clinical significance in cancer, *Cancer Invest* 27, 1023-1037.
3. Ingber, D. E. (2006) Mechanical control of tissue morphogenesis during embryological development, *Int J Dev Biol* 50, 255-266.
4. Krieg, M., Arboleda-Estudillo, Y., Puech, P. H., Kafer, J., Graner, F., Muller, D. J., and Heisenberg, C. P. (2008) Tensile forces govern germ-layer organization in zebrafish, *Nat Cell Biol* 10, 429-436.
5. Discher, D. E., Janmey, P., and Wang, Y. L. (2005) Tissue cells feel and respond to the stiffness of their substrate, *Science* 310, 1139-1143.
6. Hinz, B., and Gabbiani, G. (2003) Cell-matrix and cell-cell contacts of myofibroblasts: role in connective tissue remodeling, *Thromb Haemost* 90, 993-1002.
7. Albelda, S. M. (1993) Role of integrins and other cell adhesion molecules in tumor progression and metastasis, *Lab Invest* 68, 4-17.
8. Mammoto, T., and Ingber, D. E. (2010) Mechanical control of tissue and organ development, *Development* 137, 1407-1420.
9. Youssef, J., Nurse, A. K., Freund, L. B., and Morgan, J. R. (2011) Quantification of the forces driving self-assembly of three-dimensional microtissues, *Proc Natl Acad Sci USA* 108, 6993-8
10. Zemel, A., and Safran, S. A. (2007) Active self-polarization of contractile cells in asymmetrically shaped domains, *Phys Rev E Stat Nonlin Soft Matter Phys* 76, 021905.
11. Carlsson, A. E. (2006) Contractile stress generation by actomyosin gels, *Phys Rev E Stat Nonlin Soft Matter Phys* 74, 051912.
12. MacKintosh, F. C., and Levine, A. J. (2008) Nonequilibrium mechanics and dynamics of motor-activated gels, *Phys Rev Lett* 100, 018104.
13. Chen, P., and Shenoy, V. B. (2010) Strain stiffening induced by molecular motors in active crosslinked biopolymer networks *Soft Matter* 2, 355-358.
14. Timoshenko, S. P., and Goodier, J. N. (1970) *Theory of Elasticity*, 3 ed., McGraw-Hill Companies, Inc. New York, USA.
15. Tomasek, J. J., Gabbiani, G., Hinz, B., Chaponnier, C., and Brown, R. A. (2002) Myofibroblasts and mechanoregulation of connective tissue remodelling, *Nat Rev Mol Cell Biol* 3, 349-363.

16. Desmouliere, A., Chaponnier, C., and Gabbiani, G. (2005) Tissue repair, contraction, and the myofibroblast, *Wound Repair Regen* 13, 7-12.
17. Gabbiani, G. (2003) The myofibroblast in wound healing and fibrocontractive diseases, *J Pathol* 200, 500-503.
18. Hinz, B. (2009) Tissue stiffness, latent TGF-beta1 activation, and mechanical signal transduction: implications for the pathogenesis and treatment of fibrosis, *Curr Rheumatol Rep* 11, 120-126.
19. Hinz, B., Celetta, G., Tomasek, J. J., Gabbiani, G., and Chaponnier, C. (2001) Alpha-smooth muscle actin expression upregulates fibroblast contractile activity, *Mol Biol Cell* 12, 2730-2741.
20. Freyman, T. M., Yannas, I. V., Yokoo, R., and Gibson, L. J. (2001) Fibroblast contraction of a collagen-GAG matrix, *Biomaterials* 22, 2883-2891.
21. Dean, D. M., Napolitano, A. P., Youssef, J., and Morgan, J. R. (2007) Rods, tori, and honeycombs: the directed self-assembly of microtissues with prescribed microscale geometries, *Faseb J* 21, 4005-4012.
22. Omelchenko, T., Fetisova, E., Ivanova, O., Bonder, E. M., Feder, H., Vasiliev, J. M., and Gelfand, I. M. (2001) Contact interactions between epitheliocytes and fibroblasts: formation of heterotypic cadherin-containing adhesion sites is accompanied by local cytoskeletal reorganization, *Proc Natl Acad Sci USA* 98, 8632-8637.
23. Fernandez-Gonzalez, R., and Zallen, J. A. (2009) Cell mechanics and feedback regulation of actomyosin networks, *Sci Signal* 2, pe78.
24. Desmouliere, A., Geinoz, A., Gabbiani, F., and Gabbiani, G. (1993) Transforming growth factor-beta 1 induces alpha-smooth muscle actin expression in granulation tissue myofibroblasts and in quiescent and growing cultured fibroblasts, *J Cell Biol* 122, 103-111.
25. Lamouille, S., and Derynck, R. (2007) Cell size and invasion in TGF-beta-induced epithelial to mesenchymal transition is regulated by activation of the mTOR pathway, *J Cell Biol* 178, 437-451.
26. Birchmeier, C., and Gherardi, E. (1998) Developmental roles of HGF/SF and its receptor, the c-Met tyrosine kinase, *Trends Cell Biol* 8, 404-410.
27. Park, J. S., Kim, J. Y., Cho, J. Y., Kang, J. S., and Yu, Y. H. (2000) Epidermal growth factor (EGF) antagonizes transforming growth factor (TGF)-beta1-induced collagen lattice contraction by human skin fibroblasts, *Biol Pharm Bull* 23, 1517-1520.
28. Montesano, R., and Orci, L. (1988) Transforming growth factor beta stimulates collagen-matrix contraction by fibroblasts: implications for wound healing, *Proc Natl Acad Sci USA* 85, 4894-4897.
29. Chen, J., Li, H., SundarRaj, N., and Wang, J. H. (2007) Alpha-smooth muscle actin expression enhances cell traction force, *Cell Motil Cytoskeleton* 64, 248-257.
30. Roberts, A. B., Heine, U. I., Flanders, K. C., and Sporn, M. B. (1990) Transforming growth factor-beta. Major role in regulation of extracellular matrix, *Ann N Y Acad Sci* 580, 225-232.
31. Vaughan, M. B., Howard, E. W., and Tomasek, J. J. (2000) Transforming growth factor-beta1 promotes the morphological and functional differentiation of the myofibroblast, *Exp Cell Res* 257, 180-189.
32. Hinz, B., Pittet, P., Smith-Clerc, J., Chaponnier, C., and Meister, J. J. (2004) Myofibroblast development is characterized by specific cell-cell adherens junctions, *Mol Biol Cell* 15, 4310-4320.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for screening drug candidates that affect heterotypic intercellular mechanotransduction, comprising the steps of:
   a) labeling at least two types of cells with distinct intracellular fluorescent marker labels;
   b) seeding a cell culture medium with the at least two types of cells in a suspension;
   c) combining a drug candidate with the cells in suspension, and then culturing the cells in a non-adherent mold to thereby form spheroids, or culturing the cells in the non-adherent mold to form spheroids and then combining the spheroids with the drug candidate, or culturing the cells in the non-adherent mold to form spheroids while combining the cells with the drug candidate; and
   d) comparing the distribution of the at least two different types of cells to that of spheroids of essentially the same cell suspension cultured in the absence of the drug candidate.

2. The method of claim 1, wherein at least one of the types of cells is a connective tissue cell.

3. The method of claim 2, wherein the connective tissue is a fibroblast cell.

4. The method of claim 2, wherein the connective tissue is a myofibroblast cell.

5. The method of claim 1, wherein at least one of the types of cells is a parenchymal cell.

6. The method of claim 5, wherein the parenchymal cell is at least one member selected from the group consisting of an epithelial cell, a muscle cell, a neural cell, kidney cells, lung cells, cardiomyocyte cells and liver cells.

* * * * *